(12) United States Patent
Mansha et al.

(10) Patent No.: US 9,688,611 B2
(45) Date of Patent: Jun. 27, 2017

(54) SYNTHESIS OF (S)-2-ACETAMIDO-3-(4-HYDROXY-3-(3-METHYLBUT-2-ENYL) PHENYL) PROPANOIC ACID DERIVATIVES

(71) Applicant: King Fahd University of Petroleum and Minerals, Dhahran (SA)

(72) Inventors: Muhammad Mansha, Dhahran (SA); Yasir Abbas, Dhahran (SA); Nisar Ullah, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/918,658

(22) Filed: Oct. 21, 2015

(65) Prior Publication Data

US 2017/0114004 A1    Apr. 27, 2017

(51) Int. Cl.
*C07C 227/16*    (2006.01)
*A61K 31/198*    (2006.01)
*A61K 38/19*    (2006.01)

(52) U.S. Cl.
CPC .......... *C07C 227/16* (2013.01); *A61K 31/198* (2013.01); *A61K 38/191* (2013.01)

(58) Field of Classification Search
CPC .... C07C 227/16; A61K 31/198; A61K 38/191
See application file for complete search history.

(56) References Cited

U.S. PATENT DOCUMENTS

2013/0039883 A1* 2/2013 Sayers ................. A61K 31/047
424/85.1

FOREIGN PATENT DOCUMENTS

CN    102219706 B    8/2013

OTHER PUBLICATIONS

Ahmed et al., "Tyrosine Derivatives Isolated from *Streptomyces* sp IFM 10937 in a Screening Program for TRAIL-Resistance-Overcoming Activity," J. Nat. Prod. 2008, 71, 1963-1966.*
Osuna et al, "Aromatic Claisen Rearrangement of O-Prenylated Tyrosine and Model Prenyl Aryl Ethers: Computional Study of the Role of Water on Acceleration of Claisen Rearrangements," Eur. J. Org. Chem., 2013(14), 2823-2831.*
Silvia Osuna, et al., "Aromatic Claisen Rearrangements of O-Prenylated Tyrosine and Model Prenyl Aryl Ethers: Computational Study of the Role of Water on Acceleration of Claisen Rearrangements", European J Org Chem., vol. 14, May 1, 2013, 19 pages.
Firoj Ahmed, et al., "Tyrosine Derivatives Isolated from *Streptomyces* sp. IFM 10937 in a Screening Program for TRAIL-Resistance-Overcoming Activity", Journal of Natural Products, vol. 71, No. 11, 2008, pp. 1963-1966.
John A. McIntosh, et al., "Enzymatic Basis of Ribosomal Peptide Prenylation in Cyanobacteria", Journal of the American Chemical Society, vol. 133, 2011, pp. 13698-13705.

* cited by examiner

*Primary Examiner* — Mark Luderer
(74) *Attorney, Agent, or Firm* — Oblon, McClelland, Maier & Neustadt, L.L.P.

(57) ABSTRACT

A method for producing a compound of formula (I) or a pharmaceutically acceptable salt, solvate, tautomer or stereoisomer, such as compound 1 and compound 2 is disclosed. The method proceeds through an O-allylated tyrosine-based compound, such as compound 3 and preferably comprises [3,3] sigmatropic Claisen rearrangement and olefin cross metathesis reactions. In addition, a pharmaceutical composition comprising a compound of formula (I) a tumor necrosis factor (TNF) related apoptosis inducing ligand (TRAIL) and a pharmaceutically acceptable carrier or excipient is disclosed.

20 Claims, 1 Drawing Sheet

SYNTHESIS OF (S)-2-ACETAMIDO-3-(4-HYDROXY-3-(3-METHYLBUT-2-ENYL)PHENYL) PROPANOIC ACID DERIVATIVES

BACKGROUND OF THE INVENTION

Technical Field

The present disclosure relates to compounds having a tyrosine-based structure with prenyl group substitution and bearing properties for abrogating TRAIL resistance. A method for producing the compounds, and a pharmaceutical composition comprising one or more of the compounds is presented.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cancers are genetic diseases that result from the deregulation of cell growth and cell death pathways due to genomic alterations. Apoptosis, the process of programmed cell death, is a genetically programmed biochemical process that removes unwanted cells and maintains tissue homeostasis. Tumor necrosis factor related apoptosis inducing ligand (TRAIL), a tumor necrosis factor (TNF) family member, activates apoptotic pathways selectively in cancer cells through binding on the death receptors, DR4 and DR5 [Pitti, R. M.; Marsters, S. A.; Ruppert, S.; Donahue, C. J.; Moore, A.; Ashkenazi, A. *J. Biol. Chem.* 1996, 271, 12687-12690.; and Wiley, S. R.; Schooley, K.; Smolak, P. J.; Din, W. S.; Huang, C-P.; Nicholl, J. K.; Sutherland, G. R.; Smith, T. D.; Rauch, C.; Smith, C. A.; Goodwin, R. G. *Immunity* 1995, 3, 673-682.; and Ashkenazi, A. *Nat. Rev. Cancer* 2002, 2, 420-430.; and Pan, G.; Ni, J.; Wei, Y. F.; Yu, G.; Gentz, R.; Dixit, V. M. *Science* 1997, 277, 815-818.; and Schneider, P.; Thome, M.; Burns, K.; Bodmer, J. L.; Hofmann, K.; Kataoka, T.; Holler, N.; Tschopp, J. *Immunity* 1997, 7, 831-836.; and Chaudhary, P. M.; Eby, M.; Jasmin, A.; Bookwalter, A.; Murray, J.; Hood, L. *Immunity* 1997, 7, 821-830.; and Wu, G. S.; Burns, T. F.; McDonald, E. R 3$^{rd}$.; Jiang, W.; Meng, R.; Krantz, I. D.; Kao, G.; Gan, D. D.; Zhou, J. Y.; Muschel, R.; Hamilton, S. R.; Spinner, N. B.; Markowitz, S.; Wu, G.; el-Deiry, W. S. *Nat. Genet.* 1997, 17, 141-143. —each incorporated herein by reference in its entirety]. After initiation by the death receptor pathway, TRAIL-induced apoptosis results in activation of effector caspase-3, death-inducing signaling complex (DISC) formation and proteolytic activation of caspase-8 [Ashkenazi, A.; Dixit, V. M. *Curr. Opin. Cell. Biol.* 1999, 11, 255-260. —incorporated herein by reference in its entirety].

TRAIL has emerged as an attractive antineoplastic agent due to its remarkable ability to selectively kill tumoral cells while leaving normal cells unscathed [Ishibashi, M.; Ohtsuki, T. *Med. Res. Rev.* 2008, 28, 688-714. —incorporated herein by reference in its entirety]. Unlike the other members of the TNF superfamily, in vivo administration of TRAIL has been proven to be safe [Ahmed, F.; Toume, K.; Sadhu, S. K.; Ohtsuki, T.; Arai, M. A.; Ishibashi, M. *Org. Biomol. Chem.* 2010, 8, 3696-3703. —incorporated herein by reference in its entirety]. However, in the case of highly malignant tumors, a reasonable number of cancer cells have intrinsic or acquired resistance to TRAIL induced apoptosis [Zhang, L.; Fang, B. *Cancer Gene Ther.* 2005, 12, 228-237. —incorporated herein by reference in its entirety]. Therefore, the discovery of compounds that can abrogate TRAIL resistance has attracted a great deal of attention in anticancer drug discovery.

In a recent study, bioassay-guided fractionation of *Streptomyces* sp. IFM 10937, has led to the isolation of a new tyrosine derivative, compound 1 (FIG. 1) [Ahmed, F.; Ohtsuki, T.; Aida, W.; Ishibashi, M. *J. Nat. Prod.* 2008, 71, 1963-1966. —incorporated herein by reference in its entirety]. Compound 1 was evaluated for its activity in overcoming TRAIL resistance in AGS (human gastric adenocarcinoma) cells. Combined treatment of 75 or 150 μM of compound 1 and 100 ng/mL TRAIL with AGS cell lines reduced cell viability to 77±7% and 67±5% of control levels (p<0.01), respectively, which suggested a possible synergism between the two agents.

In view of the forgoing and ongoing efforts towards the total synthesis of bioactive natural products [Arafeh, K. M.; Ullah, N. *Nat. Prod. Commun.* 2009, 4, 925-926.; and Ullah, N.; Arafeh, K. M. *Tetrahedron Lett.* 2009, 50, 158-160.; and Ullah, N.; Haladu, S. A. *Nat. Prod. Commun.* 2010, 5, 1077-1080.; and Ullah, N.; Haladu, S. A.; Moosa, B. A. *Tetrahedron Lett.* 2011, 52, 212-214. —each incorporated herein by reference in its entirety] one object of the present disclosure is to provide a method for producing compounds of formula (I), such as compound 1 and compound 2, which bear TRAIL resistance abrogating properties via robust, reproducible and economical synthetic methods including rearrangement and olefin cross metathesis. A further aim of the present disclosure is pharmaceutical compositions comprising compounds of formula (I) such as compound 1 and compound 2.

BRIEF SUMMARY OF THE INVENTION

According to a first aspect, the present disclosure relates to a method for producing a compound of formula (I)

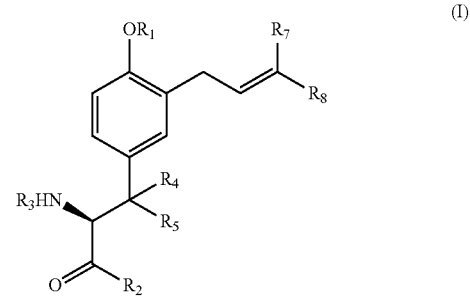

or a pharmaceutically acceptable salt, solvate, tautomer, or stereoisomer thereof wherein i) $R_1$ is —H, —$R_6$, or —$COR_6$ ii) $R_2$ is —OH, —$NH_2$, —$OR_6$, —$NHR_6$, or —$N_6R_6$ iii) $R_3$ is —H, —$R_6$, —$COR_6$, —$COOR_6$, or —$SO_2R_6$ iv) $R_4$ and $R_5$ are independently —H, —OH, —$NH_2$, —$OR_6$, —$NHR_6$, —$NR_6R_6$ v) each $R_6$ is independently an optionally substituted alkyl, optionally substituted cycloalkyl, or optionally substituted aryl and vi) $R_7$ and $R_8$ are independently —$CONH_2$, —COOH, —COH, —CN, —$COR_6$, —$COOR_6$, —$CH_2OR_6$, —$CHR_6OR_6$, —$CR_6R_6OR_6$, —$CH_2NR_6R_6$, optionally substituted alkyl, optionally substituted cycloalkyl, or optionally substituted aryl with the method comprising i) rearranging an O-allylated tyrosine-based compound to form a rearranged tyrosine-based compound with an allyl group and a phenolic hydroxyl group ii) reacting the phenolic hydroxyl group of the rearranged tyrosine-based compound with an electrophile and then iii) olefin cross metathesizing the allyl group with an alkene to form the compound of formula (I).

In one embodiment $R_1$ is —H, $R_2$ is —OH, $R_3$ is —COCH$_3$, $R_4$ is —H, $R_5$ is —H, $R_7$ is —CH$_3$ and $R_8$ is —CH$_3$ and the compound of formula (I) is

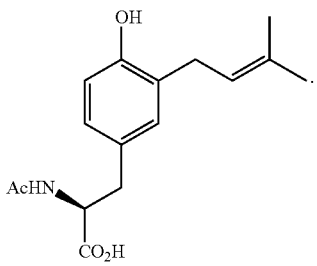

compound 1

In one embodiment $R_1$ is —H, $R_2$ is —OH, $R_3$ is —H, $R_4$ is —H, $R_5$ is —H, $R_7$ is —CH$_3$ and $R_8$ is CH$_3$ and the compound of formula (I) is

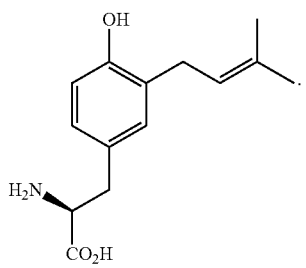

compound 2

In one embodiment, the olefin cross metathesizing comprises reacting the allyl group with the alkene in the presence of at least one catalyst selected from the group consisting of a Schrock catalyst, a first generation Grubbs' catalyst, a second generation Grubbs' catalyst, a Hoveyda-Grubbs catalyst, and a fast initiating third generation Grubbs' catalyst.

In one embodiment, at least one catalyst is present in a molar percentage of less than 10 mol % relative to the total moles of the allyl group.

In one embodiment, the olefin cross metathesizing is performed at temperatures of at least 20° C.

In one embodiment, the alkene is a compound of formula (II)

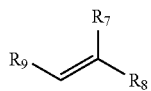

(II)

wherein i) $R_7$ and $R_8$ are independently —CONH$_2$, —COOH, —COH, —CN, —COR$_{10}$, —COOR$_{10}$, —CH$_2$OR$_{10}$, —CHR$_{10}$OR$_{10}$, —CR$_{10}$R$_{10}$OR$_{10}$, —CH$_2$NR$_{10}$R$_{10}$, optionally substituted alkyl, optionally substituted cycloalkyl, or optionally substituted aryl, ii) $R_9$ is independently an optionally substituted alkyl, optionally substituted cycloalkyl, or optionally substituted aryl, and iii) each $R_{10}$ is independently an optionally substituted alkyl, optionally substituted cycloalkyl, or optionally substituted aryl.

In one embodiment, the rearranging is a [3,3]-sigmatropic rearrangement and/or a Claisen rearrangement.

In one embodiment, the rearranging is performed in a microwave reactor at a temperature above 175° C.

In one embodiment, the O-allylated tyrosine-based compound is

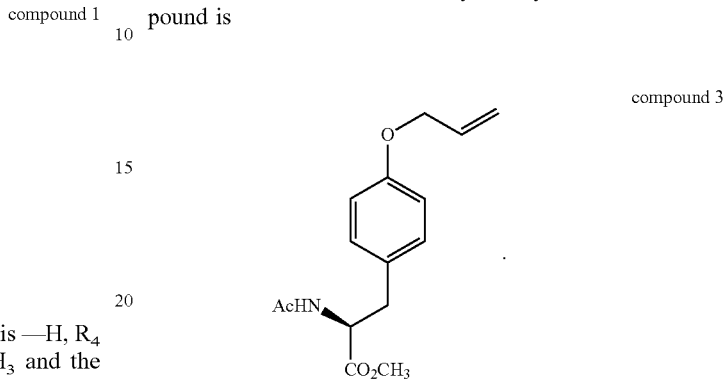

compound 3

In one embodiment, the method further comprises forming the O-allylated tyrosine-based compound, compound 3, from L-tyrosine or a pharmaceutically acceptable salt, solvate, tautomer, or stereoisomer thereof.

In one embodiment, the method further comprises saponifying with a base after olefin cross metathesizing to produce the compound of formula (I) which is

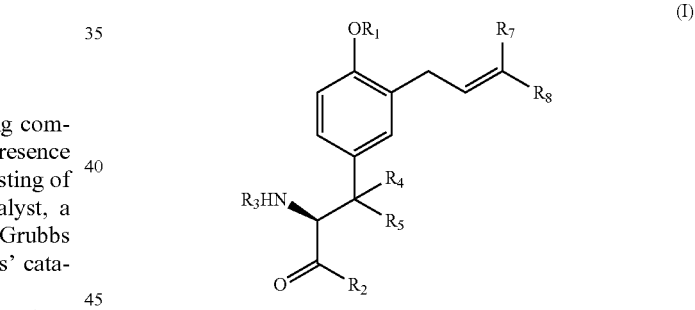

(I)

or a pharmaceutically acceptable salt, solvate, tautomer, or stereoisomer thereof wherein i) $R_1$ is —H ii) $R_2$ is —OH iii) $R_3$ is —H, —R$_6$, —COR$_6$, —COOR$_6$, or —SO$_2$R$_6$ iv) $R_4$ and $R_5$ are independently —H, —OH, —NH$_2$, —OR$_6$, —NHR$_6$, —NR$_6$R$_6$ v) each $R_6$ is independently an optionally substituted alkyl, optionally substituted cycloalkyl, or optionally substituted aryl and vi) $R_7$ and $R_8$ are independently —CONH$_2$, —COOH, —COH, —CN, —COR$_E$, —COOR$_6$, —CH$_2$OR$_6$, —CHR$_6$OR$_6$, —CR$_6$R$_6$OR$_6$, —CH$_2$NR$_6$R$_6$, optionally substituted alkyl, optionally substituted cycloalkyl, or optionally substituted aryl.

In one embodiment, the base is lithium hydroxide.

In one embodiment, the electrophile is acetic anhydride, an alkyl halide, an aryl halide, a dialkyl sulfate, a dialkyl carbonate, and alkyl triflate, a diazoalkane, or an aryne.

In one embodiment, the method has an overall yield of greater than 40% from the O-allylated tyrosine-based compound to the compound of formula (I).

In one embodiment, the rearranging has a yield of greater than 65% from the O-allylated tyrosine-based compound to the rearranged tyrosine-based compound.

In one embodiment, the method has a yield of greater than 75% from the rearranged tyrosine-based compound to the compound of formula (I).

According to a second aspect, the present disclosure relates to a pharmaceutical composition comprising i) a compound of formula (I) ii) tumor necrosis factor (TNF) related apoptosis inducing ligand (TRAIL) and iii) a pharmaceutically acceptable carrier or excipient.

In one embodiment, the pharmaceutical composition comprises less than 10% by weight of the pharmaceutically acceptable carrier or excipient relative to the total weight of the pharmaceutical composition.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
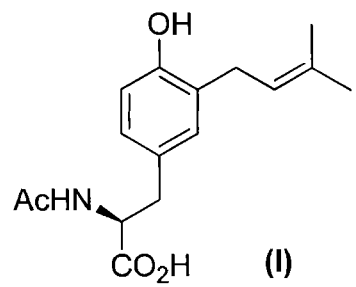
FIG. 1 is the chemical structure of a compound of formula (I), compound 1.

Referring now to the drawings, wherein, like reference numerals designate identical or corresponding parts throughout the several views. Embodiments of the present disclosure will now be described more fully hereinafter with reference to the accompanying drawings, in which some, but not all of the embodiments of the disclosure are shown. The present disclosure will be better understood with reference to the following definitions.

According to a first aspect, the present disclosure relates to a method for producing a compound of formula (I)

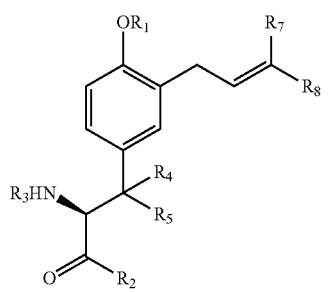

or a pharmaceutically acceptable salt, solvate, tautomer or stereoisomer thereof, wherein $R_1$ is —H, —$R_6$ or —$COR_6$, $R_2$ is —OH, —$NH_2$, —$OR_6$, —$NHR_6$, or —$NR_6R_6$, $R_3$ is —H, —$R_6$, —$COR_6$, —$COOR_6$, or —$SO_2R_6$, $R_4$ and $R_5$ are independently —H, —OH, —$NH_2$, —$OR_6$, —$NHR_6$, —$NR_6R_6$, each $R_6$ is independently an optionally substituted alkyl, optionally substituted cycloalkyl, or optionally substituted aryl, and $R_7$ and $R_8$ are independently —$CONH_2$, —COOH, —COH, —CN, —$COR_6$, —$COOR_6$, —$CH_2OR_6$, —$CHR_6OR_6$, —$CR_6R_6OR_6$, —$CH_2NR_6R_6$, optionally substituted alkyl, optionally substituted cycloalkyl, or optionally substituted aryl.

As used herein, the phrase "pharmaceutically acceptable" refers to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit to risk ratio. Therefore, the pharmaceutical composition refers to the combination of an active agent with a carrier, inert or active, making the composition especially suitable for diagnostic or therapeutic use in vivo or ex vivo.

As used herein, the term "compound" or "complex" refers to a chemical entity, whether in the solid, liquid or gaseous phase, as well as in a crude mixture or purified and isolated form. The chemical transformations and or reactions described herein are envisaged to proceed via standard laboratory and experimental techniques in regard to performing the reaction as well as standard purification, isolation and characterization protocols known to those skilled in the art.

As used herein, the term "pharmaceutically acceptable salts" refers to derivatives of the disclosed compounds wherein the parent compound is modified by making acid or base salts thereof. Exemplary pharmaceutically acceptable salts include, but are not limited, mineral or organic acid salts of basic groups such as amines, and alkali or organic salts of acidic groups such as carboxylic acids. The pharmaceutically acceptable salts include, but are not limited to, the conventional non-toxic salts or the quaternary ammonium salts of the parent compound formed, for example, from non-toxic inorganic or organic acids. Exemplary conventional non-toxic salts include those derived from inorganic acids including, but not limited to, hydrochloric, hydrobromic, sulfuric, sulfamic, phosphoric, and nitric; and those derived from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic and mixtures thereof and the like. Further, salts of carboxylic acid containing compounds may include cations such as lithium, sodium, potassium, magnesium, quaternary ammonium, and the like. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally non-aqueous media like ether, ethyl acetate, ethanol, isopropanol, or acetonitrile are preferred.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by the chemical reaction of tautomerization or tautomerism. The reaction commonly results in the formal migration of a hydrogen atom or proton, accompanied by a switch of a single bond and adjacent double bond. Tautomerism is a special case of structural isomerism and because of the rapid interconversion; tautomers are generally considered to be the same chemical compound. In solutions in which tatomerization is possible, a chemical equilibrium of the tautomers will be reached. The exact ratio of the tautomers depends on several factors including, but not limited to, temperature, solven and pH. Exemplary common tautomeric pairs include, but are not limited to, ketone and enol, enamine and imine, ketene and ynol, nitroso and oxime, amide and imidic acid, lactam and lactim (an amide and imidic acid tautomerism in heterocyclic rings), enamine and enamine and anomers of reducing sugars.

Prototropy or prototropic tautomerism refers to the relocation of a proton. Prototropy may be considered a subset of acid base behavior. Prototropic tautomers are sets of isomeric protonation states with the same empirical formula and total charge. Tautomerizations may be catalyzed by bases (deprotonation, formation of an enolate or delocalized anion), and protonation at a different position of the anion) and/or acids (protonation, formation of a delocalized cation and deprotonation at a different position adjacent to the cation). Two additional subcategories of tautomerization include annular tautomerism, wherein a proton can occupy two or more positions of a heterocyclic system, and ring-chain tautomerism, wherein the movement of a proton is accompanied by a change from an open structure to a ring. Valence tautomerism is a type of tautomerism in which single and/or double bonds are rapidly formed and ruptured, without migration of atoms or groups. It is distinct from prototropic tautomerism, and involves processes with rapid reorganization of bonding electrons, such as open and closed forms of certain heterocycles, such as azide-tetrazole or mesoionic munchnone-acylamino ketene. Valence tautomerism requires a change in molecular geometry unlike canonical resonance structures or mesomers. In terms of the present disclosure, the tautomerism may refer to prototropic tautomerism, annular tautomerism, ring-chain tautomerism, valence tautomerism, or both.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connections or their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enatiomeric optical isomers. Diastereomers seldom have the same physical properties. In terms of the present disclosure, stereoisomers may refer to enantiomers, diastereomers or both.

Conformers (rotamers), or conformational isomerism refers to a form of isomerism that describes the phenomenon of molecules with the same structural formula butwith different shapes due to rotations about one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation about the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the invention can generally be prepared by conventional techniques known to those skilled in the art or by processes and methods analogous to those described herein, using an appropriate isotopically labeled reagent in place of the non-labeled reagent otherwise employed.

In one embodiment, the method of the present disclosure may produce a compound of formula (I) or a pharmaceutically acceptable prodrug thereof. As used herein, the term "prodrug" refers to an agent that is converted into a biologically active form in vivo. As used herein, "pharmaceutically acceptable prodrugs" refer to a compound that is metabolized, for example hydrolyzed or oxidized, in the host to form the compound of formula (I) and or to form the pharmaceutical composition of the present disclosure. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound.

Prodrugs include, but are not limited to compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxy, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl, or arylakyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified, refers to both branched and straight chain saturated aliphatic primary, secondary, and/or tertiary hydrocarbon of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, or phosphonate or mixtures thereof. The substituted moiety may be either protected or unprotected as necessary, and as known to those skilled in the art.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantly. Branched cycloalkyl groups such as exemplary 1-methylcyclopropyl and 2-methycyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, naphthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate, or phosphonate or mixtures thereof. The substituted moiety may be either protected or unprotected as necessary, and as known to those skilled in the art.

In a preferred embodiment, the method of the present disclosure produces the compound of formula (I) or a pharmaceutically acceptable salt, solvate, tautomer or stereoisomer thereof wherein $R_1$ is —H, $R_2$ is —OH, $R_3$ is —COCH$_3$, $R_4$ is —H, $R_5$ is —H, $R_7$ is —CH$_3$ and $R_8$ is —CH$_3$ and the compound of formula (I) is

Figure 2:
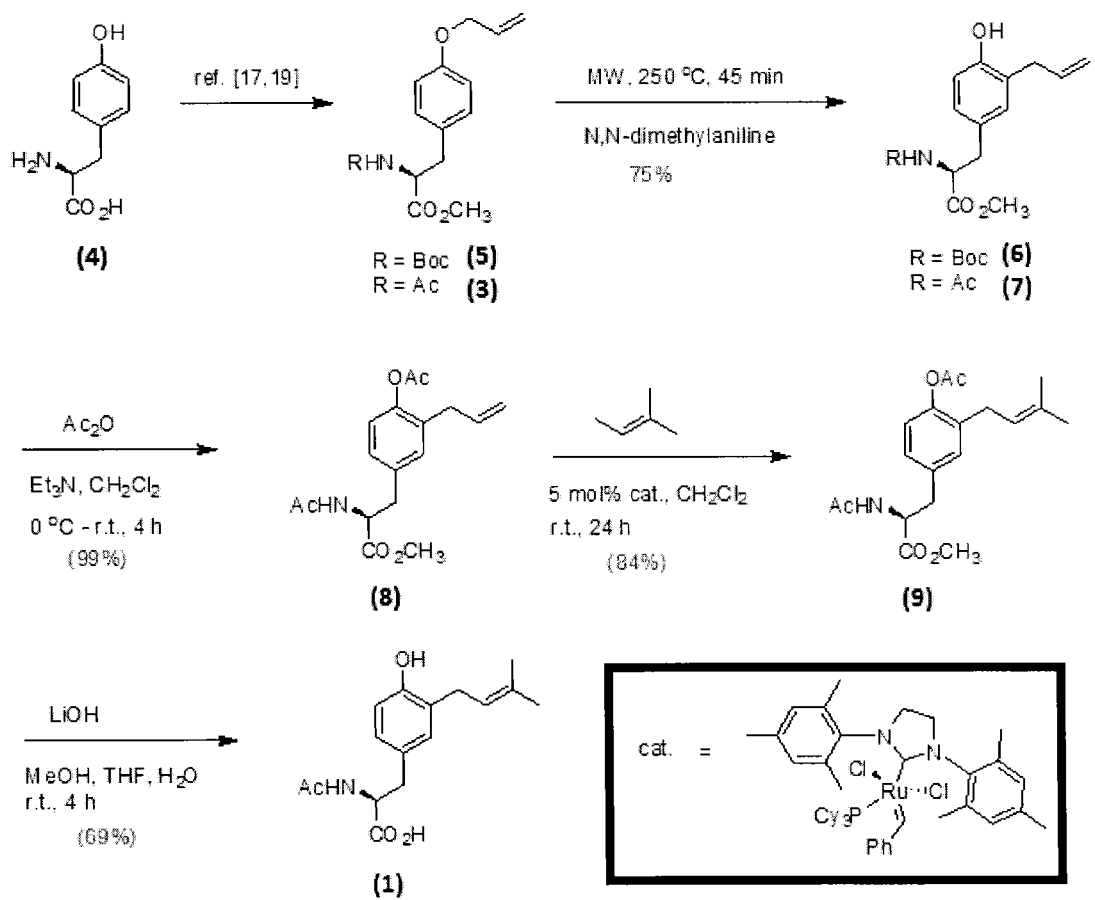
FIG. 2 is a synthetic scheme for the production of a compound of formula (I), compound 1, from the O-allylated tyrosine compound 3, and the production of a compound of formula (I), compound 1, from L-tyrosine compound 4, via the O-allylated tyrosine compound 3.

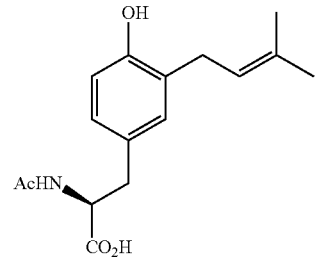

compound 1 (FIG. 1 and FIG. 2)

In a preferred embodiment, the method the present disclosure produces the compound of formula (I) or a pharmaceutically acceptable salt, solvate, tautomer or stereoisomer thereof wherein $R_1$ is —H, $R_2$ is —OH, $R_3$ is —H, $R_4$ is —H, $R_5$ is —H, $R_7$ is —CH$_3$ and $R_8$ is CH$_3$ and the compound of formula (I) is

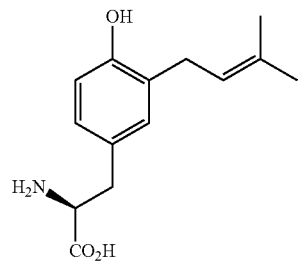

compound 2

In one step of the method, an O-allylated tyrosine-based compound is rearranged to form a rearranged tyrosine-based compound with an allyl group and phenolic hydroxyl group. In a preferred embodiment, the rearrangement reaction is a sigmatropic rearrangement, preferably a [3,3] sigmatropic rearrangement, preferably a Claisen rearrangement, more preferably an aromatic Claisen rearrangement, more preferably an ortho aromatic Claisen rearrangement.

A sigmatropic reaction in organic chemistry is a pericyclic reaction wherein the net result is one σ-bond is changed to another σ-bond in an uncatalyzed intramolecular process, in this type of rearrangement reaction, a substituent moves from one part of a π-bonded system to another part in an intramolecular reaction with simultaneous rearrangement of the it system. Sigmatropic rearrangements are concisely described by an order term [i,j], which is defined as the migration of a σ-bond adjacent to one or more π systems to a new position (i–1) and (j–1) atoms removed from the original location of the σ-bond. [3,3] sigmatropic shifts are well studied sigmatropic rearrangements and the Woodward-Hoffman rules predict that these six electron reactions proceed suprafcially, via a Huckel topology transition state.

The Claisen rearrangement is a carbon-carbon bond forming chemical reaction wherein the heating of an allyl vinyl ether will initiate a [3,3] sigmatropic rearrangement to give a γ,δ-unsaturated carbonyl. The aromatic variation of the Claisen rearrangement is the [3,3] sigmatropic rearrangement of an allyl phenyl ether to an intermediate which quickly tautomerizes to an ortho-substituted phenol. Meta-substitution affects the regioselectivity of the ortho rearrangement. With the meta constituent in the 3-position, electron withdrawing functional groups generally move the side chain to the 2-position while electron donating groups typically shift it to the 6-position. If the ortho-position is substituted then the reaction typically goes to the para position with retention of configuration. Exemplary variations of the Claisen rearrangement include, but are limited to, the Bellus-Claisen rearrangement, the Eschenmoser-Claisen rearrangement, the Ireland-Claisen rearrangement, the Johnson-Claisen rearrangement, and the Photo-Claisen rearrangement. Exemplary hetero-Claisens include, but are not limited to the Aza-Claisen, chromium oxidation, the Chem-Mapp reaction, the Overman rearrangement, and the zwitterionic Claisen rearrangement.

The Claisen rearrangement is an exothermic concerted pericyclic reaction showing a suprafacial reaction pathway. There are substantial solvent effects in the Claisen reactions. Generally, more polar solvents tend to accelerate the reaction to a greater extent with hydrogen bonding solvents giving high rate constants. In a preferred embodiment, the rearrangement of the present disclosure is performed in a polar aprotic solvent such as tetrahydrofuran, ethyl acetate, acetone, dimethylformamide, N,N-dimethylaniline, N,N-diethylaniline, acetonitrile, dimethyl sulfoxide, nitromethane, or propylene carbonate, preferably dimethylformamide, N,N-dimethylaniline, or dimethyl sulfoxide, most preferably N,N-dimethyl aniline. In a preferred embodiment, the rearrangement of the present disclosure is performed in a polar aprotic solvent having a boiling point of greater than 120° C., preferably greater than 140° C., preferably greater than 150° C., preferably greater than 160° C., preferably greater than 180° C., preferably greater than 190° C., preferably greater than 200° C. It is equally envisaged that the rearrangement of the present disclosure may be adapted to be performed in a polar protic solvent, a non-polar solvent or mixtures thereof as well as neat without solvent.

In a preferred embodiment, the rearrangement of the present disclosure is performed at elevated temperatures. The heating may be provided by conventional heating (i.e. furnace or oil bath) or microwave heating. Microwave chemistry refers to the science of applying microwave radiation to chemical reactions. Microwaves act as high frequency electric fields and will generally heat any material containing mobile electric charges, such as polar molecules in a solvent or conducting ions in a solid. Under conventional thermal heating conditions the rearrangement is performed at reflux, preferably at temperatures of 150-275° C., preferably 175-250° C., preferably 200-250° C. In a preferred embodiment, the rearrangement of the present disclosure is performed in a microwave reactor under microwave irradiation at a temperature above 175° C., preferably above 200° C., preferably above 225° C., preferably above 250° C., preferably above 275° C. at 200-300 W, preferably 225-275 W, preferably 230-270 W, preferably 240-260 W, preferably 250-260 W with a reaction time of up to 4 hours, preferably up to 2 hours, preferably up to 1 hour, preferably up to 45 min, preferably up to 30 min. In a preferred embodiment, the rearrangement reaction of the present disclosure has a yield of 60-99%, preferably 65-95%, preferably 70-90%, preferably 70-85%, preferably 70-80% or 75% relative to the total initial moles of the O-allylated tyrosine-based compound.

In a preferred embodiment, the O-allylated tyrosine-based compound and the substrate for the rearrangement of the method of the present disclosure is

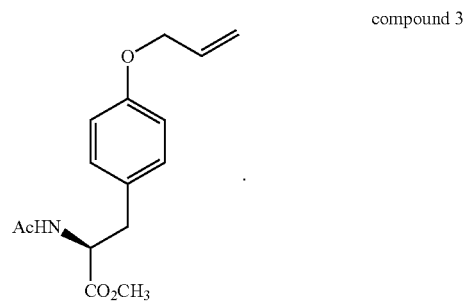 [SMILES: C=CCOc1ccc(C[C@H](NC(C)=O)C(=O)OC)cc1]

compound 3

In one embodiment, the method of the present disclosure further comprises forming the O-allylated tyrosine-based compound (i.e. compound 3) from L-tyrosine or a pharmaceutically acceptable salt, solvate, tautomer or stereoisomer thereof. In one embodiment, the conversion of L-tyrosine to the O-allylated tyrosine-based compounds may comprise the relatively straight forward and non-limiting steps of esterification, amide carbamate protection (i.e. -Boc, -Alloc, -Cbz, -Fmoc, -Troc, Teoc) and O-allylation via an allyl halide (i.e. allyl bromide, allyl chloride) or similar chemical transformations and the like. In one embodiment, derivatives of the compound of formula (I) of the present disclosure wherein $R_4$ and/or $R_5$ are not hydrogen ($R_4$ and/or $R_5 \neq$ —H), may be formed by following these same steps starting from an L-tyrosine derivative that is substituted at $R_4$ and/or $R_5$ with non-hydrogen. For example, starting with β-hydroxy tyrosine may provide compounds of formula (I) wherein $R_4$ and/or $R_5$=—OH.

In another step of the method, the phenolic hydroxyl group of the rearranged tyrosine-based compound is reacted with an electrophile. In a preferred embodiment, the electrophile is acetic anhydride, an alkyl halide, an aryl halide, a dialkyl sulfate, a dialkyl carbonate, an alkyl triflate, a diazoalkane or an aryne, preferably acetic anhydride or an alkyl halide, most preferably acetic anhydride. In a preferred embodiment, the reaction may convert the phenolic hydroxyl group to an ether including, but not limited to, a methyl ether, a methoxymethyl ether (MOM), a methoxyethoxymethyl ether (MEM), a benzyloxymethyl ether (BOM), a tetrahydropyranyl ether (THP), a benzyl ether (Bn), a p-methoxybenzyl ether (PMB), a silyl ether (trimethylsilyl ether, triethylsilyl ether, triisopropylsilyl ether, t-butyldimethylsilyl ether, t-butyldiphenylsilyl ether), an o-nitrobenzyl ether, a p-nitrobenzyl ether, a trityl ether or an ester via an electrophile including, but not limited to, an acid chloride or an anhydride (e.g. acetic anhydride, pivalic anhydride, etc.).

In a preferred embodiment, the electrophile is acetic anhydride and the reaction is an acetylation. In a preferred embodiment, the reaction is performed in a non-polar solvent such as pentane, cyclopentane, hexane, cyclohexane, benzene, toluene, 1,4-dioxane, chloroform, diethyl ether or dichloromethane, preferably dichloromethane, most preferably anhydrous dichloromethane. It is also envisaged that the reaction with an electrophile of the present disclosure may be adapted to be performed in a polar aprotic solvent, a polar protic solvent or mixtures thereof. In a preferred embodiment, reaction is performed at a temperature of 0-50° C., preferably 0-30° C., preferably 10-30° C., preferably 15-30° C., preferably 20-30° C. and has a stirred reaction time of up to 8 hr, preferably up to 4 hr, preferably up to 2 hr. In a preferred embodiment, the reaction is quantitative and preferably has a yield of 80-99%, preferably 90-99%, preferably 95-99%, preferably 97-99%, preferably 98-99% to the total initial moles of the phenolic hydroxyl group.

In another step of the method, the allyl group of the rearranged tyrosine-based compound is olefin cross metathesized with an alkene to form the compound of formula (I). Olefin metathesis refers to the organic reaction that entails the redistribution of fragments of alkenes (olefins) by the scission and regeneration of carbon-carbon double bonds. Due to the relative simplicity of olefin metathesis, it often creates fewer undesired by-products and hazardous wastes than alternative organic reactions. Exemplary types of olefin metathesis processes include, but are not limited to, cross metathesis (CM), ring-opening metathesis (ROM), ring-closing metathesis (RCM), ring-opening metathesis polymerization (ROMP), acyclic diene metathesis (ADMET), intermolecular enyne metathesis and ethenolysis.

Olefin cross metathesis is an effective alternative to other olefination methods due to the large variety of commercially available olefin starting materials and due to the high functional group tolerance. Depending on the types of olefins involved in the metathesis reaction, cross metathesis reactions may fall into one of three types including, but not limited to, chain extending which brings together two olefins to make a longer chain molecule, chain shortening which is functionally the opposite of chain extending such as ethenolysis of an internal olefin to produce terminal olefins, and functionalizing where a terminal olefin is carried through a synthetic sequence and "functionalized" at a late stage by cross metathesis with a functional olefin. In terms of the present disclosure, the olefin cross metathesis may be chain extending, chain shortening or functionalizing.

The olefin cross metathesis reaction is catalyzed by metal complexes. Traditional catalysts are prepared by a reaction of metal halides with alkylation agents, for example $WCl_6$-$EtOH$-$EtAlCl_2$. The traditional, industrial catalysts are ill-defined and used mainly for petroleum products. Modern catalysts are well-defined organometallic compounds typically from two main categories. Schrock catalysts are molybdenum (IV) and tungsten (IV) based Schrock alkylidenes and/or Schrock carbenes. Grubbs' catalysts are ruthenium (II) carbenoid complexes often modified with a chelating isopropoxystyrene ligand to form the related Hoveyda-Grubbs catalyst.

Grubbs' catalysts are a series of transition metal carbene complexes used as catalysts for olefin metathesis. In contrast to Schrock catalysts and other olefin metathesis catalysts, Grubbs' catalyst tolerate other functional groups in the alkene, are air tolerant, and are compatible with a wide range of solvents. The first well-defined ruthenium catalyst for olefin metathesis is prepared from $RuCl_2(PPh_3)_4$ and diphenylcyclopropene. This initial ruthenium catalyst was followed by first generation Grubbs catalyst, which is easily synthesized from $RuCl_2(PPh_3)_3$, phenyldiazomethane and tricyclohexylphosphine in a one-pot synthesis and often serves as a precursor to all other Grubbs type catalysts. The second generation Grubbs' catalyst is higher in activity and stable toward moisture and air. A first iteration is based on an unsaturated N-heterocyclic carbene (1,3-bis(2,4,6-trimethylphenyl)imidazole) followed by the commonly known second generation Grubbs' catalyst based on a saturated N-heterocyclic carbene (1,3-bis(2,4,6-trimethylphenyl)dihydroimidazole). In both the saturated and unsaturated cases a phosphine ligand is replaced with an N-heterocyclic carbene (NHC), characteristic of all second generation catalysts. There are many derivatives of the second generation catalyst.

In the Hoveyda-Grubbs catalysts, the benzylidiene ligands have a chelating ortho-isopropoxy group attached to the benzene rings. The ortho-isopropoxybenzylidene moiety is sometimes referred to as a Hoveyda chelate. The chelating oxygen atom replaces a phosphine ligand, which in the case of the second generation catalyst, gives a completely phosphine free structure. The Hoveyda-Grubbs catalysts are more expensive and slower to initiate than the Grubbs catalyst from which they are derived but with improved stability. Hoveyda-Grubbs catalysts are easily formed from the corresponding Grubbs catalyst by the addition of the chelating ligand and the use of a phosphine scavenger such as copper (I) chloride. The second generation Hoveyda-Grubbs catalysts can also be prepared from the first generation Hoveyda-Grubbs catalyst by the addition of the NHC. The initiation rate of the Grubbs' catalyst can be altered by replacing the phosphine ligand with more labile pyridine ligands. For example, the use of 3-bromopyridine in the fast initiating catalysts increases the initiation rate more than a million fold.

In terms of the present disclosure, the olefin cross metathesizing comprises reacting the allyl group with the alkene in the presence of at least one catalyst selected from the group consisting of a Schrock catalyst, a first generation Grubbs' catalyst, a second generation Grubbs' catalyst, a Hoveyda-Grubbs catalyst, and a fast initiating or third generation Grubbs' catalyst. Preferably the catalyst is a first generation Grubbs' catalyst, a second generation Grubb's catalyst or a Hoveyda-Grubbs catalyst, most preferably a second generation Grubb's catalyst. In a preferred embodiment, the catalyst is present in a loading or molar percentage of less than 10 mol % relative to the total initial moles of the allyl group, preferably less than 8 mol %, preferably less than 6 mol %, preferably less than 5 mol %, preferably less than 4 mol %, preferably less than 3 mol %, preferably less than 2 mol % relative to the total initial moles of the allyl group.

There are many variants and derivatives of Grubbs' catalysts and Schrock catalysts. As used herein "Schrock catalyst" is used to generally describe olefin metathesis catalysts of the Schrock type, but may include various steric and electronic substitutions, as well as ligand substitutions. As used herein "Grubbs' catalyst" is used to generally describe olefin metathesis catalysts of the Grubbs type, but may include various steric and electronic substitutions, as well as ligand substitutions. For example, focusing on NHC-Ru complexes that contain either tricyclohexylphosphine or Hoveyda-type chelating ligands this may include, but is not limited to, complexes bearing two NHC ligands, complexes bearing one NHC ligand, complexes bearing imidazole-2-ylidene or imidazolin-2-ylidene ligands (with substituents at the 1,3-positions and/or 4,5-positions), complexes bearing 1,2,4-triazol-5-ylidene ligands, complexes bearing thiazol-2-ylidene ligands, complexes bearing cyclic (alkyl)(amino)carbene ligands, complexes bearing four membered ring carbene ligands, complexes bearing 1,4,5,6-tetrandropyrimidin-2-ylidene ligands, and complexes bearing tetrahydro-1,3-diazepin-2-ylidenes ligands. For example, focusing on variations of the heterocyclic carbene ligand, the anionic ligands, the alkylidene moiety and the neutral ligand this may include, but is not limited to symmetrical, unsymmetrical and chiral hetetocyclic carbene frameworks, phosphine free heterocyclic carbene coordinated catalysts (chelating alkoxybenzylidene ligands, chelating thioether and chelating sulfoxide benzylidene ligands, mono- and bis(pyridine) coordinated catalysts, chelating quinolin- and quinoxalin-ylidenes, bidentate alkylidenes chelated through imine donors, 14-electron phosphonium alklyidenes), alkylidene variation (Fischer-type carbenes, idenylidenes, vinylidenes, cyclic ruthenium alkylidene, and other alkylidene ligands), variation of the phosphine ligand, anionic ligand variation (halides, monodentate and bidentate aryloxides, N,O-, P,O-, and O,O-bidentate ligands, carboxylates and (alkyl)sulfonates, nitrile- and isonitrile-coordinated alkylidene free catalysts) and N-heterocyclic carbene coordinated (η6-Arene) catalysts.

The direct [2+2] cycloaddition of two alkenes is formally symmetry forbidden and has a high activation energy. The accepted mechanism of transition metal alkene metathesis involves the [2+2] cycloaddition of an alkene double bond to a transition metal alkylidene to form a metallacyclobutatne intermediate. The metallacyclobutane produced can then cyclorevert to give either the original species or a new alkene and alkylidene. Interaction with the d-orbitals on a metal catalyst lowers the activation energy enough that the reaction can proceed rapidly at modest temperatures. The metathesis pathway is driven by a thermodynamic imperative and the final products are determined by the energetics of the possible products, with a distribution of products proportional to the exponential of the respective energy values. In olefin metathesis, all possible products have similar energy values (all contain an olefin). Cross metathesis is often additionally driven by the entropically favored evolution of gases (i.e. ethylene or propylene) and cross metathesis reactions may often comprise or use alpha-olefins. Thus, the product mixtures can be tuned by reaction conditions, such as gas pressure and substrate concentration. In some instances, the reaction can be run in either direction to near completion.

In a preferred embodiment, the olefin cross metathesis reaction is performed in a non-polar solvent such as pentane, cyclopentane, hexane, cyclohexane, benzene, toluene, 1,4-dioxane, chloroform, diethyl ether or dichloromethane, preferably dichloromethane. It is equally envisaged that the olefin cross metathesis of the present disclosure may be adapted to be performed in a polar aprotic solvent, a polar protic solvent or mixtures thereof. In a preferred embodiment, the olefin cross metathesis reaction is performed at a temperature of at least 20° C., preferably 20-100° C., preferably 20-80° C., preferably 20-60° C., preferably 20-40° C., preferably 20-30° C. and has a stirred reaction time of up to 48 hr, preferably up to 36 hr, preferably up to 24 hr, preferably up to 12 hr, preferably up to 10 hr, preferably up to 8 hr. The reaction may be performed outside of these parameters and still provide acceptable olefin cross metathesis product. In a preferred embodiment, the olefin cross metathesis reaction of the present disclosure has a yield of 60-99%, preferably 65-98%, preferably 70-95%, preferably 75-90%, preferably 80-90% or 85% relative to the total initial moles of the allyl group.

In a preferred embodiment, the alkene with which the allyl group is olefin cross metathesized with is a compound of formula (II)

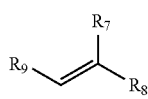
(II)

wherein i) $R_7$ and $R_8$ are independently —$CONH_2$, —COOH, —COH, —CN, —$COR_{10}$, —$COOR_{10}$, —$CH_2OR_{10}$, —$CHR_{10}OR_{10}$, —$CR_{10}R_{10}OR_{10}$, —$CH_2NR_{10}R_{10}$, optionally substituted alkyl, optionally substituted cycloalkyl, or optionally substituted aryl, ii) $R_9$ is independently an optionally substituted alkyl, optionally substituted cycloalkyl, or optionally substituted aryl, and iii) each $R_{10}$ is independently an optionally substituted alkyl, optionally substituted cycloalkyl, or optionally substituted aryl. In a most preferred embodiment, the alkene is 2-methyl-2-butene wherein $R_7$ is —$CH_3$, $R_8$ is —$CH_3$ and $R_9$ is —$CH_3$.

In a preferred embodiment, the olefin cross metathesis is performed in a manner such that the alkene is present in a molar ratio of up to 200:1 relative to the moles of the allyl group, preferably up to 100:1, preferably up to 75:1, preferably up to 60:1, preferably up to 50:1, preferably up to 40:1, preferably up to 20:1, preferably up to 10:1, preferably up to 5:1 molar ratio relative to the moles of the allyl group.

In one embodiment, the method of the present disclosure further comprises saponifying under basic condition after olefin cross metathesizing to produce the compound of formula (I) which is

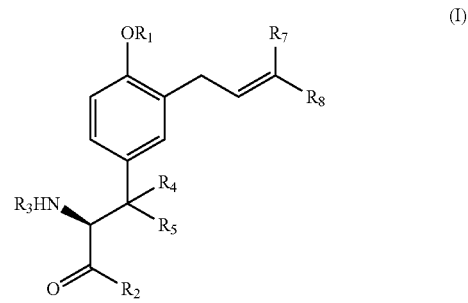
(I)

or a pharmaceutically acceptable salt, solvate, tautomer, or stereoisomer thereof wherein i) $R_1$ is —H ii) $R_2$ is —OH iii) $R_3$ is —H, —$R_6$, —$COR_6$, —$COOR_6$, or —$SO_2R_6$ iv) $R_4$ and $R_5$ are independently —H, —OH, —$NH_2$, —$OR_6$, —$NHR_6$, —$NR_6R_6$ v) each $R_6$ is independently an optionally substituted alkyl, optionally substituted cycloalkyl, or optionally substituted aryl and vi) $R_7$ and $R_8$ are independently —$CONH_2$, —COOH, —COH, —CN, —$COR_E$, —$COOR_6$, —$CH_2OR_6$, —$CHR_6OR_6$, —$CR_6R_6OR_6$, —$CH_2NR_6R_6$, optionally substituted alkyl, optionally substituted cycloalkyl, or optionally substituted aryl.

As used herein, "saponification" refers to the hydrolysis of esters using a basic solution, in a preferred embodiment the hydrolysis of an ester reclaims the phenolic hydroxyl group of the rearranged tyrosine-based compound. The mechanism by which esters are cleaved by base involves a series of equilibria. The hydroxide anion adds to the carbonyl group of the ester forming an orthoester. Expulsion of the alkoxide generates a carboxylic acid. The alkoxide ion is a strong base so that the proton is transferred from the carboxylic acid to the alkoxide ion creating an alcohol. In a preferred embodiment, the base is lithium hydroxide. In another embodiment, exemplary additional suitable bases envisaged include, but are not limited to, potassium carbonate ($K_2CO_3$), ammonia ($NH_3$), potassium cyanide (KCN), and any suitable mild base as well as enzyme hydrolysis (i.e. Lipase). In a preferred embodiment, the saponification is performed in a mixture of polar aprotic solvent and polar protic solvent (i.e. tetrahydrofuran, methanol and water, 3:1:1) with a 2-20 fold excess of base, preferably 3-10, preferably 4-8 or 5 fold excess of base and with a reaction time of less than 8 hr, preferably less than 6 hr, preferably less than 4 hr, preferably less than 2 hr.

In a preferred embodiment, the method of the present disclosure has an overall yield of greater than 40% from the O-allylated tyrosine-based compound to the compound of formula (I), preferably 40-80%, preferably 40-60%, preferably 40-50%, or 45% from the O-allylated tyrosine-based compound to the compound of formula (I). In one embodiment, in the method of the present disclosure the rearranging has a yield of greater than 65%, preferably 65-95%, preferably 70-90%, preferably 70-85%, preferably 70-80% or 75% from the O-allylated tyrosine-based compound to the rearranged tyrosine-based compound. In one embodiment, the method of the present disclosure has a yield of greater than 75%, preferably 75-95%, preferably 80-90% or 85% from the rearranged based tyrosine compound to the compound of formula (I).

According to a second aspect, the present disclosure relates to a pharmaceutical composition including i) the compound of formula (I) or a pharmaceutically acceptable salt, solvate, tautomer, or stereoisomer thereof, ii) tumor necrosis factor (TNF) related apoptosis inducing ligand (TRAIL) and iii) a pharmaceutically acceptable carrier or excipient.

In cell biology, tumor necrosis factor (TNF) related apoptosis inducing ligand (TRAIL) is a protein functioning as a ligand that induces the process of programmed cell death, apoptosis. TRAIL is a cytokine that is produced and secreted by most normal tissue cells. It causes apoptosis, primarily in tumor cells, by binding to certain death receptors. TRAIL is designated CD253 (cluster of differentiation 253) and TNFSF10 (tumor necrosis factor (ligand) superfamily, member 10). In humans, the gene that encodes TRAIL is located at chromosome 3q26, which is not close to other TNF family members. The genomic structure of the TRAIL gene spans approximately 20 kb and is composed of five exonic segments 22, 138, 42, 106, and 1245 nucleotides and four introns of approximately 8.2, 3.2, 2.3 and 2.3 kb. The TRAIL gene lacks TATA and CAAT boxes and the promoter region contains putative response elements for GATA, AP-1, C/EBP, SP-1, OCT-1, AP3, PEA3, CF-1, and ISRE.

TRAIL shows homology to other members of the tumor necrosis factor superfamily. It is composed of 281 amino acids and has characteristics of a type II transmembrane protein (i.e. no leader sequence and an internal transmembrane domain). The N-terminal cytoplasmic domain is not conserved across family members; however, the C-terminal extracellular domain is conserved and can be proteolytically cleaved from the cell surface. TRAIL forms a homotrimer that binds three receptor molecules. TRAIL binds to the death receptors DR4 (TRAIL-RI) and DR5 (TRAIL-RII). The process of apoptosis is caspase-8 dependent. Caspase-8 activates downstream effector caspases including procasspase-3, procaspase-6, and procaspase-7 leading to the activation of specific kinases. TRAIL also binds the receptors DcR1 and DcR2, which do not contain a cytoplasmic domain (DcR1) or contain a truncated death domain (DcR2). DcR1 functions as a TRAIL neutralizing decoy receptor. The cytoplasmic domain of DcR2 is functional and activates NFkappaB. In cells expressing DcR2, TRAIL binding therefore activates NFkappaB, leading to transcription of genes known to antagonize the death signaling pathway and/or to promote inflammation. TRAIL has also been shown to interact with TNFRSF10B.

In one embodiment, it is envisaged that pharmaceutical composition of the present disclosure may further comprise at least one additional member of the TNF family. Tumor necrosis factors, or the TNF family, refer to a group of cytokines that can cause cell death, apoptosis. Exemplary additional members of the TNF include, but are not limited to, tumor necrosis factor (TNF, cachectin, TNF alpha), Lymphotoxin-alpha (LT-alpha), lymphotoxin-beta (LT-beta), T cell antigen gp39 (CD40L), CD27L, CD30L, FASL, 4-1BBL, and OX40L.

Several cancer cell lines can develop resistance to TRAIL initiated apoptosis including, but not limited to, prostate cancer LNCaP cells, human gastric adenocarcinoma (AGS) cells, leukemia cells, hepatoma cells, human breast cancer cells, and human ovarian carcinoma OVCAR3 cells. It is further envisaged that compounds of formula (I) that reverse or limit TRAIL resistance are advantageous and the treatment with compounds of formula (I) in combination with TRAIL may possess activity in sensitizing TRAIL-resistant cells. In another embodiment, a method of treating cancer is envisioned comprising treatment with the pharmaceutical composition of the present disclosure. In another embodiment, the method may comprise combination therapy wherein the compound of formula (I), or a pharmaceutical composition thereof, is administered and subsequently and separately the TRAIL ligand, or a pharmaceutical composition thereof, is administered.

As used herein, the phrase "pharmaceutically acceptable carrier or excipient" refers to a pharmaceutically acceptable material, composition or vehicle such as a liquid or solid filler, diluent, binder, manufacturing aid (e.g. lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Exemplary materials which can serve as pharmaceutically acceptable carriers include, but are not limited to: (1) sugars, such as lactose, glucose and sucrose; (2) starches, such as corn starch and potato starch; (3) cellulose, and its derivatives, such as sodium carboxy methyl cellulose, ethyl cellulose and cellulose acetate; (4) powdered tragancanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesers, polycarbonates and/or polyanhydrides; (22) other nontoxic compatible substances employed in pharmaceutical formulations and mixtures thereof.

In another embodiment, wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the compositions described herein. Exemplary pharmaceutically acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In another embodiment, the pharmaceutically acceptable carrier or excipient is a binder. As used herein, "binders" refers to materials that hold the ingredients in a tablet together. Binders ensure that tablets and granules can be formed with the required mechanical strength, and give volume to low active dose tablets. Exemplary pharmaceutically acceptable binders include, but are not limited to: (1) saccharides and their derivatives, such as sucrose, lactose, starches, cellulose or modified cellulose such as microcrystalline cellulose, carboxy methyl cellulose, and cellulose ethers such as hydroxypropyl cellulose (HPC), and sugar alcohols such as xylitol, sorbitol or maltitol; (2) proteins such as gelatin; and (3) synthetic polymers including polyvinylpyrrolidone (PVP) and polyethylene glycol (PEG).

Binders can be classified according to their application. Solution binders are dissolved in a solvent (i.e. water or alcohol in wet granulation processes). Exemplary solution binders include, but are not limited to, gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Exemplary dry binders include, but are not limited to, cellulose, methyl cellulose, polyvinylpyrrolidone and polyethylene glycol. In terms of the present disclosure, the pharmaceutically acceptable carrier or excipient may be a solution binder, a dry binder or mixtures thereof.

In one embodiment, the pharmaceutical composition is formulated for systemic administration. Formulations of the present invention include, but are not limited to, those suitable for oral, nasal, topical (i.e. buccal and sublingual), rectal, vaginal, and/or parenteral administration. The formulations may conveniently be presented in unit dosage form and may be prepared by any methods well known in the art of pharmacy. As used herein, the "active ingredient" of the pharmaceutical composition of the present disclosure may refer to the compound of formula (I), the TRAIL ligand, or both. The amount of active ingredient, compound of formula (I) and/or TRAIL ligand, which can be combined with a carrier material to produce a single dosage form, will vary depending upon the host being treated as well as the particular mode of administration. The amount of active ingredient, compound of formula (I) and/or TRAIL ligand, which can be combined with a carrier material to produce a single dosage form, will generally be that amount of the compound of formula (I) and TRAIL ligand which produces a therapeutic effect, and which does not cause systemic toxicity, for example through a cytokine cascade.

In one embodiment, the pharmaceutical composition of the present disclosure comprises a single compound of formula (I). In another embodiment, the pharmaceutical composition comprises more than one compound of formula (I), preferably 1-10, preferably 1-5, preferably 1-3, preferably 1-2 compounds of formula (I). In a preferred embodiment, the compound of formula (I) is present in a 1:1 molar ratio relative to the TRAIL ligand. In another embodiment the compound of formula (I) may be present in a 0.1:1, preferably 0.25:1, preferably 0.5:1, preferably 1:1, preferably 1.25:1, preferably 1.5:1, preferably 1.75:1, preferably 2:1, preferably 3:1, preferably 5:1, preferably 10:1, preferably 20:1 molar ratio relative to the TRAIL ligand.

In one embodiment, the pharmaceutical composition comprises 1-99.9 wt %, preferably 10-99 wt %, more preferably 20-95 wt %, more preferably 30-90 wt %, more preferably 40-90 wt %, more preferably 50-90 wt %, more preferably 60-90 wt %, more preferably 70-90 wt %, more preferably 80-90 wt % of the active ingredient (i.e. compound of formula (I), TRAIL ligand, or both) relative to the total weight of the pharmaceutical composition. In one embodiment, the pharmaceutical composition comprises 0.1-10 wt %, preferably 0.25-8 wt %, preferably 0.5-6 wt %, preferably 0.75-4 wt %, preferably 1-2 wt % of the pharmaceutically acceptable carrier or excipient relative to the total weight of the pharmaceutical composition.

In another embodiment, the pharmaceutical composition of the present disclosure may further comprise one or more additional pharmaceutically active ingredients that may also reverse and/or slow the resistance to TRAIL ligands. Exemplary additional pharmaceutically active ingredients include, but are not limited to Bcl-2 antagonist, c-FLIP inhibitors, inhibitor of apoptosis protein (IAP) antagonists, epigallocatechin-3-gallate, resveratrol, curcumin, a dihydrofavonol (BB-1), tunicamycin, sulforaphane, etc. and mixtures thereof.

The examples below are intended to further illustrate methods and protocols for preparing and characterizing the compounds of formula (I) of the present disclosure. Further, they are intended to illustrate assessing the properties of these compounds. They are not intended to limit the scope of the claims.

EXAMPLE 1

Characterization of Prepared Compounds

Elemental analysis was carried out on a Perkin-Elmer Elemental Analyzer Series 11 model 2400 (Perkin-Elmer Inc. USA). Infra-red (IR) spectra were recorded on a Thermo Scientific Nicolet 6700 FT-IR Perkin Elmer 16F PC FTIR spectrophotometer (Thermo Scientific USA). $^1$H and $^{13}$C nuclear magnetic resonance (NMR) spectra were measured in $CDCl_3$ and $CD_3OD$ using tetramethylsilane (TMS) as internal standard on a Jeol JNM-LA 500 MHz spectrometer (Jeol USA Inc.). Analytical thin layer chromatography (TLC) was carried out on silica gel 60 F254 plates (E. Merck); column chromatography was carried out on silica gel (200-400 mesh, E. merck).

EXAMPLE 2

Synthesis of (S)-Methyl 2-acetamido-3-(3-allyl-4-hydroxyphenyl)propanoate (Compound 7, $C_{15}H_{19}NO_4$)

Synthesis of desired compound 1 (FIG. 1 and FIG. 2) was envisaged from the olefin cross metathesis reaction of intermediate compound 6, which in turn, was to be synthesized from Claisen rearrangement of intermediate compound 5 (see FIG. 2). Thus, L-tyrosine compound 4 was converted to intermediate compound 5 by the operations of esterification, N-boc protection and O-allylation based on procedures known in the literature [Navarro, R.; Perrino, M. P.; Prucker, O.; Jurgen. R. *Langmuir* 2013, 29, 10932-10939. —incorporated herein by reference in its entirety].

However, Claisen rearrangement of intermediate compound 5 either under thermal or microwave irradiation conditions at different temperatures, using N,N-dimethylaniline or DMF as solvents were unsuccessful. For example, under thermal conditions, the reaction in N,N-dimethylaniline or DMF at reflux resulted in intact starting material, whereas heating compound 5 neat at elevated temperatures led to the decomposition of compound 5, with no desired product formation. Likewise, under microwave conditions, reaction at lower temperatures (200° C., 250 W, 1 hr.) in DMF resulted in unchanged compound 5, whereas heating the reaction at higher temperatures (250° C., 250 W, 45 min.) in N,N-dimethylaniline led to the deprotection of the N-Boc group. Deprotection of the N-Boc group under microwave conditions using mild base or under thermolytic conditions are well known [Dandepally, S. R.; Williams, A. L. *Tetrahedron Lett.* 2009, 50, 1071-1074. —incorporated herein by reference in its entirety]. To address the N-Boc deprotection problem attention turned to preparing the N-acetyl derivative compound 3 which in turn was synthesized from intermediate compound 4 according to a known literature procedure [Boyle, T. M.; Bremner, J. B.; Coates, J.; Deadman, J.; Keller, P. A.; Pyne, S. G.; Rhodes, D. I. *Tetrahedron* 2008, 64, 11270-11290. —incorporated herein by reference in its entirety].

Claisen rearrangement of intermediate compound 3 in N,N-dimethylaniline under microwave irradiation at 250° C. gave the desired rearranged phenol compound 7 in excellent yield (75%). A microwave reaction vessel containing a solution of aryl ether compound 3 (0.75 g, 2.70 mmol) in N,N-dimethylaniline (4 mL) was degassed by gently bubbling nitrogen through the solution for 1 min. The vessel was then placed inside a CEM Discover S-Class microwave synthesizer, where it was exposed to microwaves at 250° C. (260 W) for 2 hr. After completion of the reaction, the mixture was diluted with ethyl acetate (50 mL) and extracted with 3M hydrochloric acid (3×10 mL). The organic layer was washed successively with sodium hydrogen carbonate (15 mL) and brine (10 mL), dried over anhydrous sodium sulfate, filtered, and concentrated under vacuum. Column chromatography purification of the crude yellow oily material, eluting with ethyl acetate:hexanes (1:1) yielded compound 7 as a pale yellow solid (0.56 g, 75%). Yield: 0.56 g, 75%; mp 91-92° C.; $[\alpha]_D^{25}$ +25.95 (c. 1.15, CHCl$_3$); IR (neat): 3418, 3300, 3081, 3006, 2956, 1717, 1662, 1510, 1432, 1209, 1121 cm$^{-1}$; $^1$H NMR (CDCl$_3$, 500 MHz): δ 1.92 (s, 3H, NCOCH$_3$), 2.96 (dd, 2H), 3.27 (m, 2H), 3.66 (s, 3H, OCH$_3$), 4.76 (m, 1H), 4.99-5.03 (m, 2H), 5.90 (m, 1H), 5.99 (d, 1H, J=7.9 Hz, NH), 6.62 (m, 1H, aromatics), 6.72 (m, 2H, aromatics); $^{13}$C NMR (CDCl$_3$, 500 MHz): δ 23.05, 34.46, 37.05, 52.35, 53.31, 115.64, 116.07, 125.92, 127.26, 128.13, 131.04, 136.46, 153.39, 170.05, 172.29. Anal. calcd. for C$_{15}$H$_{19}$NO$_4$: C, 64.97; H, 6.91; N, 5.05. Found: C, 64.93; H, 6.94; N, 5.01.

EXAMPLE 3

Synthesis of (S)-Methyl 2-acetamido-3-(4-acetoxy-3-allylphenyl)propanoate (Compound 8, C$_{17}$H$_{21}$NO$_5$)

Acetylation of intermediate compound 7 under standard conditions rendered compound 8 in a very high yield. Triethylamine (0.75 mL, 5.41 mmol) was added to a solution of compound 7 (0.5 g, 1.80 mmol) in anhydrous dichloromethane (15 mL) at 0° C. After being stirred for 10 min., acetic anhydride (0.35 mL, 3.60 mmol) was added dropwise and the reaction was stirred for 2 hr. at room temperature. To the mixture was added ethyl acetate (30 mL) and it was washed successively with saturated sodium hydrogen carbonate (15 mL) and brine (10 mL). The organic layer was dried over anhydrous sodium sulfate and evaporated under vacuum to obtain compound 8 as an off-white solid (0.57 g, 99%). Yield: 0.57 g, 99%; mp 104° C.; $[\alpha]_D^{25}$ +56.6 (c. 1.0, CHCl$_3$); IR (neat): 3311, 3086, 2948, 1740, 1649, 1639, 1543, 1497, 1433, 1371, 1202, 1185, 1166 cm$^{-1}$; $^1$H NMR (CDCl$_3$, 500 MHz): δ 1.99 (s, 3H, NCOCH$_3$), 2.29 (s, 3H, COCH$_3$), 3.10 (t, 2H, J=5.5 Hz), 3.25 (d, 2H, J=6.7 Hz), 3.72 (s, 3H, OCH$_3$), 4.86 (m, 1H), 5.03-5.09 (m, 2H), 5.85 (m, 1H), 5.89 (d, 1H, J=7.9 Hz, NH), 6.96 (m, 3H, aromatics); $^{13}$C NMR (CDCl$_3$, 500 MHz): δ 23.18, 29.71, 34.45, 37.16, 52.38, 53.06, 116.47, 122.47, 128.18, 131.23, 132.03, 133.70, 135.70, 148.01, 169.35, 169.61, 171.94. Anal. calcd. for C$_{17}$H$_{21}$NO$_5$: C, 63.94; H, 6.63; N, 4.39. Found: C, 63.90; H, 6.68; N, 4.32.

EXAMPLE 4

Synthesis of (S)-Methyl 2-acetamido-3-(4-acetoxy-3-(3-methylbut-2-enyl)phenyl)propanoate (Compound 9, C$_{19}$H$_{25}$NO$_5$)

Olefin cross metathesis reaction between intermediate compound 8 and 2-methyl-2-butene, using second generation Grubbs' catalyst yielded the desired compound 9 in excellent yield (84%). It is noteworthy that O-prenylation of O-deallylated compound 3 followed by Claisen rearrangement could possibly give access to the O-deacetylated compound 9. However, such O-prenylation would have required palladium catalyzed reaction between deallylated compound 3 with commercially unavailable isobutyl-2-methyl-3-butene-2-ylcarbonate [Moran, W. J.; Rodriguez, A. *RSC Adv.* 2011, 1, 33-35. —incorporated herein by reference in its entirety]. O-prenylation of tyrosines in proteins have recently been accomplished with prenyltransferase LynF, an enzyme from the TruF family [McIntosh, J. A.; Donia, M. S.; Nair, S. K.; Schmidt, E. W. *J. Am. Chem. Soc.* 2011, 133, 13698-13705.; and Osuna, S.; Kim, S.; Bollot, G.; Houk, K. N. *Eur. J. Org. Chem.* 2013, 14, 2823-2831. —each incorporated herein by reference in its entirety].

To a solution of compound 8 (0.23 g, 0.72 mmol) in anhydrous dichloromethane (36 mL) was added successively 2-methyl-2-butene (4 mL) and Grubb's second generation catalyst (0.018 g, 0.021 mmol) under a nitrogen atmosphere. The solution was stirred for 24 hr. at room temperature and concentrated under vacuum. Column chromatography of the crude dark brown oily material eluting with ethyl acetate:hexanes (2:3) gave compound 9 as a light yellow solid (0.21 g, 84%). Yield: 0.21 g, 84%; mp 81-82° C.; $[\alpha]_D^{25}$ –59.7 (c. 0.22, CHCl$_3$). IR (neat): 3288, 3061, 2951, 1735, 1649, 1539, 1492, 1370, 1185, 1164 cm$^{-1}$; $^1$H NMR (CDCl$_3$, 500 MHz): δ 1.69 (s, 3H), 1.74 (s, 3H), 1.99 (s, 3H, NCOCH$_3$), 2.30 (s, 3H, COCH$_3$), 3.10 (m, 2H), 3.25 (d, 2H, J=7.3 Hz), 3.72 (s, 3H, OCH$_3$), 4.87 (m, 1H), 5.29 (m, 1H), 5.92 (d, 1H, J=9.7 Hz, NH), 6.93 (m, 3H, aromatics); $^{13}$C NMR (CDCl$_3$, 500 MHz): δ 17.82, 23.14, 25.77, 28.59, 29.71, 37.15, 52.31, 53.03, 121.38, 122.31, 127.76, 130.83, 133.41, 133.61, 147.96, 169.41, 169.59, 171.96. Anal. calcd. for C$_{19}$H$_{25}$NO$_5$: C, 65.69; H, 7.25; N, 4.03. Found: C, 65.63; H, 7.30; N, 3.97.

EXAMPLE 5

Synthesis of (S)-2-Acetamido-3-(4-hydroxy-3-(3-methylbut-2-enyl)phenyl)propanoic Acid (Compound 1, C$_{16}$H$_{21}$NO$_4$)

Exposure of compound 9 under basic conditions at room temperature ultimately produced the desired compound 1 in 43% overall yield from compound 3. All the spectral data of compound 1 matched with those of the previously isolated material. To a solution of compound 9 (0.16 g, 0.46 mmol) in a mixture of tetrahydrofuran, methanol and water (10 mL, in 3:1:1:1 ratio) was added lithium hydroxide monohydrate (0.096 g, 2.3 mmol) and the mixture was stirred for 3 hr. at room temperature. The solvent was evaporated and the residue was diluted with chloroform (20 mL) and washed with 1M hydrochloric acid (3 mL). The organic layer was dried over anhydrous sodium sulfate, concentrated under vacuum and passed over a plug of silica, eluting with methanol:dichloromethane (0.5:9.5) to afford compound 1 as a colorless solid (0.092 g, 69%). The spectral data of compound 1 coincided with literature values [Ahmed, F.; Ohtsuki, T.; Aida, W.; Ishibashi, M. J. Nat. Prod. 2008, 71, 1963-1966. —incorporated herein by reference in its entirety].

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for producing a compound of formula (I)

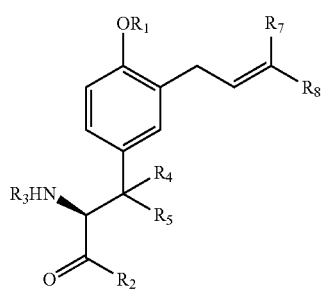

a pharmaceutically acceptable salt, solvate, tautomer, stereoisomer or combination thereof;
wherein $R_1$ is an optionally substituted alkyl, optionally substituted cycloalkyl, optionally substituted aryl or —$COR_6$;
$R_2$ is —OH, —$NH_2$, $OR_6$, —$NHR_6$, or —$NR_6R_6$;
$R_3$ is —H, —$R_6$, —$COR_6$, —$COOR_6$, or —$SO_2R_6$;
$R_4$ and $R_5$ are independently —H, —OH, —$NH_2$, —$OR_6$, —$NHR_6$, —$NR_6R_6$;
each $R_6$ is independently an optionally substituted alkyl, optionally substituted cycloalkyl, or optionally substituted aryl;
$R_7$ and $R_8$ are independently —$CONH_2$, —COOH, —COH, —CN, $COR_6$, —$COOR_6$, —$CH_2OR_6$, —$CHR_6OR_6$, —$CR_6R_6OR_6$, —$CH_2NR_6R_6$, optionally substituted alkyl, optionally substituted cycloalkyl, or optionally substituted aryl;
the method comprising:
rearranging an O-allylated tyrosine-based compound of the formula

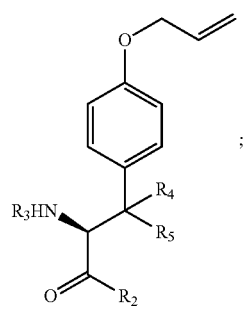

to form a rearranged tyrosine-based compound having an allyl group and a phenolic hydroxyl group of the formula

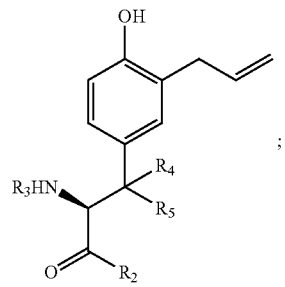

reacting the phenolic hydroxyl group of the rearranged tyrosine-based compound with an electrophile; then
olefin cross metathesizing the allyl group with an alkene to form the compound of formula (I).

2. The method of claim 1, wherein the olefin cross metathesizing comprises reacting the allyl group with the alkene in the presence of at least one catalyst selected from the group consisting of a Schrock catalyst, a first generation Grubbs' catalyst, a second generation Grubbs' catalyst, a Hoveyda-Grubbs catalyst, and a fast initiating third generation Grubbs' catalyst.

3. The method of claim 2, wherein at least one catalyst is present in a molar percentage of less than 10 mol % relative to the total moles of the allyl group.

4. The method of claim 1, wherein the olefin cross metathesizing is performed at temperatures of at least 20° C.

5. The method of claim 1, wherein the alkene is a compound of formula (II)

wherein $R_7$ and $R_8$ are independently —$CONH_2$, —COOH, —COH, $COR_{10}$, —$COOR_{10}$, —$CH_2OR_{10}$, —$CHR_{10}OR_{10}$, —$CR_{10}R_{10}OR_{10}$, —$CH_2NR_{10}R_{10}$, optionally substituted alkyl, optionally substituted cycloalkyl, or optionally substituted aryl;
$R_9$ is an optionally substituted alkyl, optionally substituted cycloalkyl, or optionally substituted aryl; and
each $R_{10}$ is independently an optionally substituted alkyl, optionally substituted cycloalkyl, or optionally substituted aryl.

6. The method of claim 1, wherein the rearranging is a [3,3]-sigmatropic rearrangement.

7. The method of claim 1, wherein the rearranging is performed in a microwave reactor at a temperature above 175° C.

8. The method of claim 1, wherein the rearranging is performed in a polar aprotic solvent having a boiling point of greater than 120° C.

9. The method of claim 1, wherein the O-allylated tyrosine-based compound is

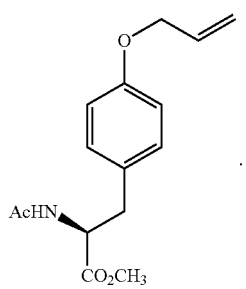

compound 3

10. The method of claim 1, further comprising forming the O-allylated tyrosine-based compound from L-tyrosine or a pharmaceutically acceptable salt, solvate, tautomer, or stereoisomer thereof.

11. The method of claim 1, further comprising saponifying with a base the compound of formula (I) after olefin cross metathesizing to produce a compound of the formula

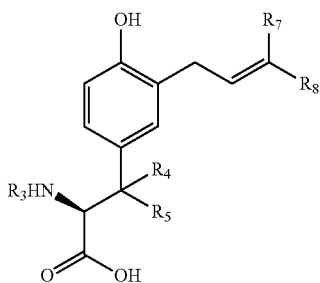

or a pharmaceutically acceptable salt, solvate, tautomer, or stereoisomer thereof;
wherein
$R_3$ is —H, —$R_6$, —$COR_6$, —$COOR_6$, or —$SO_2R_6$,
$R_4$ and $R_5$ are independently —H, —OH, —$NH_2$, —$OR_6$, —$NHR_6$, —$NR_6R_6$;
each $R_6$ is independently an optionally substituted alkyl, optionally substituted cycloalkyl, or optionally substituted aryl; and
$R_7$ and $R_8$ are independently —$CONH_2$, —COOH, —COH, —CN, —$COR_6$, —$COOR_6$, —$CH_2OR_6$, —$CHR_6OR_6$, —$CR_6R_6OR_6$, —$CH_2NR_6R_6$, optionally substituted alkyl, optionally substituted cycloalkyl, or optionally substituted aryl.

12. The method of claim 11, wherein the base is lithium hydroxide.

13. The method of claim 11, wherein the compound of formula (I) is

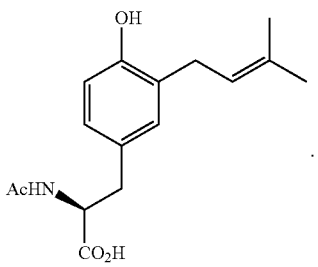

compound 1

14. The method of claim 11, wherein the compound of formula (I) is

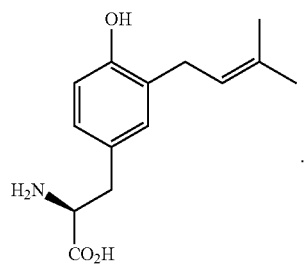

compound 2

15. The method of claim 1, wherein the electrophile is acetic anhydride, an alkyl halide, an aryl halide, a dialkyl sulfate, a dialkyl carbonate, an alkyl triflate, a diazoalkane, or an aryne.

16. The method of claim 1, which has an overall yield of greater than 40% from the O-allylated tyrosine-based compound to the compound of formula (I).

17. The method of claim 1, wherein the rearranging has a yield of greater than 65% from the O-allylated tyrosine-based compound to the rearranged tyrosine-based compound.

18. The method of claim 1, which has a yield of greater than 75% from the rearranged tyrosine-based compound to the compound of formula (I).

19. The method of claim 1, wherein $R_1$, each $R_6$, $R_7$, and $R_8$ are independently a $C_1$-$C_{10}$ alkyl, a $C_1$-$C_{10}$ cycloalkyl, or a $C_1$-$C_{10}$ aryl; and
wherein $R_1$, each $R_6$, $R_7$, and $R_8$ may be substituted with at least one substituent selected from the group consisting of a halo substituent, a hydroxy substituent, an alkoxy substituent, an oxo substituent, an amino substituent, a thiol substituent, a carbamyl substituent, and a heterocycle substituent.

20. The method of claim 11, wherein each $R_6$, $R_7$, and $R_8$ are independently a $C_1$-$C_{10}$ alkyl, a $C_1$-$C_{10}$ cycloalkyl, or a $C_1$-$C_{10}$ aryl; and
wherein each $R_6$, $R_7$, and $R_8$ may be substituted with at least one substituent selected from the group consisting of a halo substituent, a hydroxy substituent, an alkoxy substituent, an oxo substituent, an amino substituent, a thiol substituent, a carbamyl substituent, and a heterocycle substituent.

* * * * *